US012195531B2

(12) United States Patent
Getts et al.

(10) Patent No.: US 12,195,531 B2
(45) Date of Patent: Jan. 14, 2025

(54) CELLULAR DELIVERY OF DNA INTERCALATING AGENTS (71) Applicants: CODE BIOTHERAPEUTICS, INC., Hatfield, PA (US); Lankenau Institute of Medical Research, Wynnewood, PA (US)

(72) Inventors: Robert C. Getts, Collegeville, PA (US); James Kadushin, Gilbertsville, PA (US); Mindy George-Weinstein, Wynnewood, PA (US); Jacquelyn Gerhart, Wynnewood, PA (US); Emanuela Dylgjeri, Hatfield, PA (US); Kelly Rhodes, Hatfield, PA (US)

(73) Assignees: CODE BIOTHERAPEUTICS, INC., Hatfield, PA (US); Lankenau Institute of Medical Research, Wynnewood, PA (US)

(*) Notice: Subject to any disclaimer, the term of this patent is extended or adjusted under 35 U.S.C. 154(b) by 1006 days.

(21) Appl. No.: 16/568,702

(22) Filed: Sep. 12, 2019

(65) Prior Publication Data
US 2020/0148763 A1 May 14, 2020

Related U.S. Application Data (60) Continuation of application No. 15/631,226, filed on Jun. 23, 2017, now abandoned, which is a division of application No. 14/778,716, filed as application No. PCT/US2014/031192 on Mar. 19, 2014, now abandoned.

(60) Provisional application No. 61/803,863, filed on Mar. 21, 2013.

(51) Int. Cl.
| *C07K 16/28* | (2006.01) |
| *A61K 9/51* | (2006.01) |
| *A61K 31/704* | (2006.01) |
| *A61K 31/713* | (2006.01) |
| *A61K 47/54* | (2017.01) |
| *A61K 47/62* | (2017.01) |
| *A61K 47/68* | (2017.01) |
| *A61K 47/69* | (2017.01) |

(52) U.S. Cl.
CPC .............. *C07K 16/28* (2013.01); *A61K 9/513* (2013.01); *A61K 31/704* (2013.01); *A61K 31/713* (2013.01); *A61K 47/549* (2017.08); *A61K 47/62* (2017.08); *A61K 47/6849* (2017.08); *A61K 47/6859* (2017.08); *A61K 47/6925* (2017.08); *Y02A 50/30* (2018.01)

(58) Field of Classification Search
CPC ...... A61K 47/54; A61K 47/543; C07K 16/22; C07K 16/28; C07K 16/2803; C07K 16/2851; C07K 2317/24
See application file for complete search history.

(56) References Cited

U.S. PATENT DOCUMENTS

| 3,641,235 A | 2/1972 | Rozman |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,959,078 A | 5/1976 | Guire |
| 3,966,897 A | 6/1976 | Renn et al. |
| 3,984,533 A | 10/1976 | Uzgiris |
| 3,996,345 A | 12/1976 | Ullman et al. |
| 4,034,074 A | 7/1977 | Miles |
| 4,094,647 A | 6/1978 | Deutsch et al. |
| 4,098,876 A | 7/1978 | Piasio et al. |
| 4,168,146 A | 9/1979 | Grubb et al. |
| 4,196,281 A | 4/1980 | Hearst et al. |
| 4,299,916 A | 11/1981 | Litman et al. |
| 4,347,312 A | 8/1982 | Brown et al. |
| 4,366,241 A | 12/1982 | Tom et al. |
| 4,391,904 A | 7/1983 | Litman et al. |
| 4,425,438 A | 1/1984 | Bauman et al. |
| 4,517,288 A | 5/1985 | Giegel et al. |
| 4,639,425 A | 1/1987 | Baier |
| 4,666,828 A | 5/1987 | Gusella |

(Continued)

FOREIGN PATENT DOCUMENTS

| EP | 0149168 A1 | 7/1985 |
| EP | 0250137 A2 | 12/1987 |

(Continued)

OTHER PUBLICATIONS

Abderrezak A, Bourassa P, Mandeville J-S, Sedaghat-Herati R, Tajmir-Riahi H-A. "Dendrimers Bind Antioxidant Polyphenols and cisPlatin Drug," PLoS One (2012) 7(3): e33102. (Year: 2012).*

(Continued)

*Primary Examiner* — Michael P Cohen
(74) *Attorney, Agent, or Firm* — Goodwin Procter LLP (57) ABSTRACT

Compositions and methods for targeted delivery of active agents to cells are provided. The compositions comprise a wholly or partially double-stranded synthetic DNA carrier, and an active agent intercalated in double-stranded portions of the DNA carrier. The DNA carrier may also be linked to a targeting agent. The compositions are useful for delivering an active agent into a targeted cell type, for example a cytotoxic agent.

17 Claims, 4 Drawing Sheets

Specification includes a Sequence Listing.

(56) References Cited

U.S. PATENT DOCUMENTS

| | | | |
|---|---|---|---|
| 4,683,202 A | 7/1987 | Mullis | |
| 4,695,554 A | 9/1987 | O'Connell et al. | |
| 4,703,017 A | 10/1987 | Campbell et al. | |
| 4,743,560 A | 5/1988 | Campbell et al. | |
| 4,801,531 A | 1/1989 | Frossard | |
| 4,857,453 A | 8/1989 | Ullman et al. | |
| 4,879,219 A | 11/1989 | Wands et al. | |
| 4,956,302 A | 9/1990 | Gordon et al. | |
| 4,960,691 A | 10/1990 | Gordon et al. | |
| 5,011,771 A | 4/1991 | Bellet et al. | |
| 5,073,484 A | 12/1991 | Swanson et al. | |
| 5,075,078 A | 12/1991 | Osikowicz et al. | |
| 5,120,643 A | 6/1992 | Ching et al. | |
| 5,141,875 A | 8/1992 | Kelton et al. | |
| 5,168,053 A | 12/1992 | Altman et al. | |
| 5,175,270 A | 12/1992 | Nilsen et al. | |
| 5,192,659 A | 3/1993 | Simons | |
| 5,252,496 A | 10/1993 | Kang et al. | |
| 5,272,057 A | 12/1993 | Smulson et al. | |
| 5,275,785 A | 1/1994 | May et al. | |
| 5,281,521 A | 1/1994 | Trojanowski et al. | |
| 5,416,016 A | 5/1995 | Low et al. | |
| 5,484,904 A | 1/1996 | Nilsen et al. | |
| 5,487,973 A | 1/1996 | Nilsen et al. | |
| 5,504,013 A | 4/1996 | Senior | |
| 5,514,602 A | 5/1996 | Brooks, Jr. et al. | |
| 5,580,859 A | 12/1996 | Felgner et al. | |
| 5,591,645 A | 1/1997 | Rosenstein | |
| 5,602,040 A | 2/1997 | May et al. | |
| 5,653,979 A | 8/1997 | Muzykantov et al. | |
| 5,656,448 A | 8/1997 | Kang et al. | |
| 5,712,170 A | 1/1998 | Kouvonen et al. | |
| 5,846,737 A | 12/1998 | Kang | |
| 6,017,767 A | 1/2000 | Chandler | |
| 6,046,038 A | 4/2000 | Nilsen | |
| 6,072,043 A | 6/2000 | Nilsen | |
| 6,110,687 A | 8/2000 | Nilsen | |
| 6,117,631 A | 9/2000 | Nilsen | |
| 6,156,271 A | 12/2000 | May | |
| 6,180,357 B1 | 1/2001 | Young et al. | |
| 6,187,269 B1 | 2/2001 | Lancesseur et al. | |
| 6,187,598 B1 | 2/2001 | May et al. | |
| 6,274,723 B1 * | 8/2001 | Nilsen | C12Q 1/682 |
| | | | 536/2 |
| 6,319,676 B1 | 11/2001 | Nazareth et al. | |
| 6,335,435 B1 | 1/2002 | Shimamoto et al. | |
| 6,352,862 B1 | 3/2002 | Davis et al. | |
| 6,399,398 B1 | 6/2002 | Cunningham et al. | |
| 6,485,982 B1 | 11/2002 | Charlton | |
| 6,488,927 B2 | 12/2002 | Muzykantov et al. | |
| 6,528,631 B1 | 3/2003 | Cook et al. | |
| 6,534,281 B2 | 3/2003 | Kitajima et al. | |
| 6,656,730 B1 | 12/2003 | Manoharan | |
| 6,656,744 B2 | 12/2003 | Pronovost et al. | |
| RE38,430 E | 2/2004 | Rosenstein | |
| 6,770,487 B2 | 8/2004 | Crosby | |
| 6,773,928 B1 | 8/2004 | Yin et al. | |
| 6,822,086 B1 | 11/2004 | Papisov | |
| 6,861,514 B2 | 3/2005 | Cook et al. | |
| 6,919,439 B2 | 7/2005 | Manoharan et al. | |
| 7,041,287 B2 | 5/2006 | Muzykantov et al. | |
| 7,144,742 B2 | 12/2006 | Boehringer et al. | |
| 7,157,087 B2 | 1/2007 | Muzykantov et al. | |
| 7,172,760 B2 | 2/2007 | Muzykantov et al. | |
| 7,175,992 B2 | 2/2007 | Fong | |
| 7,189,522 B2 | 3/2007 | Esfandiari | |
| RE39,664 E | 5/2007 | Gordon et al. | |
| 7,223,544 B2 | 5/2007 | Luo et al. | |
| 7,238,538 B2 | 7/2007 | Freitag et al. | |
| 7,258,837 B2 | 8/2007 | Yager et al. | |
| 7,317,532 B2 | 1/2008 | Sharrock et al. | |
| 7,674,466 B2 | 3/2010 | Muzykantov et al. | |
| 7,691,997 B2 | 4/2010 | Khvorova et al. | |
| 7,879,597 B2 | 2/2011 | Esfandiari | |
| 9,651,549 B2 | 5/2017 | Casta et al. | |
| 9,707,299 B2 | 7/2017 | Muro-Galindo et al. | |
| 2001/0036460 A1 | 11/2001 | Sawicki | |
| 2002/0001580 A1 | 1/2002 | Hermonat et al. | |
| 2002/0072060 A1 | 6/2002 | Getts et al. | |
| 2003/0224490 A1 | 12/2003 | Dessain et al. | |
| 2004/0023248 A1 | 2/2004 | O'Malley | |
| 2004/0157330 A1 | 8/2004 | Sheridan et al. | |
| 2004/0171571 A1 | 9/2004 | Krieg et al. | |
| 2004/0220084 A1 | 11/2004 | Sandhu | |
| 2004/0249178 A1 | 12/2004 | Vargeese et al. | |
| 2005/0089890 A1 | 4/2005 | Cubicciotti | |
| 2005/0130180 A1 | 6/2005 | Luo et al. | |
| 2005/0215507 A1 | 9/2005 | Anderson et al. | |
| 2005/0281845 A1 | 12/2005 | Bachmann et al. | |
| 2006/0040879 A1 | 2/2006 | Kosak | |
| 2006/0160098 A1 | 7/2006 | Zak et al. | |
| 2006/0168670 A1 | 7/2006 | Lee et al. | |
| 2006/0228404 A1 | 10/2006 | Anderson et al. | |
| 2006/0246035 A1 | 11/2006 | Ahluwalia et al. | |
| 2007/0065451 A1 | 3/2007 | Muzykantov et al. | |
| 2007/0173473 A1 | 7/2007 | McSwiggen et al. | |
| 2007/0225213 A1 * | 9/2007 | Kosak | A61K 47/60 |
| | | | 424/85.4 |
| 2008/0050389 A1 | 2/2008 | Muzykantov et al. | |
| 2008/0145440 A1 | 6/2008 | Cho et al. | |
| 2008/0242851 A1 | 10/2008 | Khvorova et al. | |
| 2009/0011956 A1 | 1/2009 | Yin et al. | |
| 2009/0012022 A1 | 1/2009 | Milner et al. | |
| 2009/0130104 A1 | 5/2009 | Muzykantov et al. | |
| 2009/0234109 A1 | 9/2009 | Han et al. | |
| 2009/0297479 A1 | 12/2009 | Ariizumi et al. | |
| 2010/0112725 A1 | 5/2010 | Babu et al. | |
| 2010/0129437 A1 | 5/2010 | Gaillard | |
| 2010/0136614 A1 | 6/2010 | Luo et al. | |
| 2010/0151005 A1 | 6/2010 | Muro-Galindo et al. | |
| 2010/0190179 A1 | 7/2010 | Nilsen | |
| 2010/0323018 A1 | 12/2010 | Irvine et al. | |
| 2011/0160090 A1 | 6/2011 | Cary | |
| 2011/0256054 A1 * | 10/2011 | Menko | A61P 27/02 |
| | | | 424/178.1 |
| 2012/0122800 A1 | 5/2012 | Kadushin et al. | |
| 2012/0149647 A1 | 6/2012 | Brody et al. | |
| 2013/0018086 A1 | 1/2013 | Goldberg | |
| 2013/0171740 A1 | 7/2013 | Sakakibara | |
| 2014/0017704 A1 | 1/2014 | Casta et al. | |
| 2014/0074219 A1 | 3/2014 | Hingston et al. | |
| 2014/0127255 A1 | 5/2014 | Fearon et al. | |
| 2014/0212503 A1 | 7/2014 | Lee et al. | |
| 2015/0037358 A1 | 2/2015 | George-Weinstein et al. | |
| 2015/0177235 A1 | 6/2015 | Casta et al. | |
| 2015/0272980 A1 | 10/2015 | Rodrigueza et al. | |
| 2015/0359907 A1 | 12/2015 | Getts et al. | |
| 2016/0051693 A1 | 2/2016 | Getts et al. | |

FOREIGN PATENT DOCUMENTS

| | | | |
|---|---|---|---|
| EP | 0323605 A2 | 7/1989 | |
| EP | 404097 A2 | 12/1990 | |
| EP | 586590 A1 | 3/1994 | |
| EP | 1319179 A2 | 6/2003 | |
| GB | 1526708 A | 9/1978 | |
| JP | 2001503517 A | 3/2001 | |
| JP | 2001512034 A | 8/2001 | |
| JP | 2004505892 A | 2/2004 | |
| JP | 2005529606 A | 10/2005 | |
| JP | 2008195613 A | 8/2008 | |
| JP | 2011530537 A | 12/2011 | |
| JP | 2013520516 A | 6/2013 | |
| JP | 2015522265 A | 8/2015 | |
| WO | 1987002671 A1 | 5/1987 | |
| WO | 9010716 A1 | 9/1990 | |
| WO | 9207065 A1 | 4/1992 | |
| WO | 1993011161 A1 | 6/1993 | |
| WO | 1995024221 A1 | 9/1995 | |
| WO | 1996030047 A1 | 10/1996 | |
| WO | 1996034629 A1 | 11/1996 | |
| WO | WO-9634629 A1 * | 11/1996 | A61K 31/704 |
| WO | 9818488 A1 | 5/1998 | |
| WO | 9906595 A1 | 2/1999 | |

(56) References Cited

FOREIGN PATENT DOCUMENTS

| | | | |
|---|---|---|---|
| WO | 9940438 A1 | 8/1999 | |
| WO | 1999045960 A1 | 9/1999 | |
| WO | 1999059611 A1 | 11/1999 | |
| WO | 2000007625 A1 | 2/2000 | |
| WO | 2001087350 A2 | 11/2001 | |
| WO | 03033735 A2 | 4/2003 | |
| WO | 2004072117 A2 | 8/2004 | |
| WO | 2004100885 A2 | 11/2004 | |
| WO | 2005005957 A2 | 1/2005 | |
| WO | 2005113571 A2 | 12/2005 | |
| WO | 2006098804 A2 | 9/2006 | |
| WO | 2006099191 A2 | 9/2006 | |
| WO | 2006128152 A2 | 11/2006 | |
| WO | 2008039206 A2 | 4/2008 | |
| WO | WO-2008147526 A1 * | 12/2008 | ........... A61K 47/549 |
| WO | 2009018500 A1 | 2/2009 | |
| WO | 2009080832 A1 | 7/2009 | |
| WO | 2009086552 A1 | 7/2009 | |
| WO | 2009137055 A1 | 11/2009 | |
| WO | 2010017544 A2 | 2/2010 | |
| WO | 2010045518 A1 | 4/2010 | |
| WO | 2010065920 A1 | 6/2010 | |
| WO | 2010128087 A2 | 11/2010 | |
| WO | 2011103074 A1 | 8/2011 | |
| WO | 2011106481 A1 | 9/2011 | |
| WO | 2012032794 A1 | 3/2012 | |
| WO | 2012061402 A2 | 5/2012 | |
| WO | 2012145469 A1 | 10/2012 | |
| WO | 2013134768 A1 | 9/2013 | |
| WO | 2014012077 A1 | 1/2014 | |
| WO | 2014121050 A1 | 8/2014 | |
| WO | 2014153394 A1 | 9/2014 | |

OTHER PUBLICATIONS

Gerhart, J., et al. "Epiblast cells that express MyoD recruit pluripotent cells to the skeletal muscle lineage." J Cell Biol. Mar. 1, 2004 ; 164(5):739-46. Epub Feb. 23, 2004.
Gerhart, J., et al. "MyoD-positive epiblast cells regulate skeletal muscle differentiation in the embryo." J Cell Biol. Oct. 23, 2006;175(2):283-92.
Gerhart, J., et al. "Noggin producing, MyoD-positive cells are crucial for eye development." Dev Biol. Dec. 1, 2009;336(1):30-41. Epub Sep. 22, 2009.
Gerhart, J., et al. "Tracking and ablating subpopulations of epiblast cells in the chick embryo." Biol Proced Online. Sep. 1, 2008 ; 10:74-82.
Gharzi et al., "Plasticity of hair follicle dermal cells in wound healing and induction", Exp. Dermatol., vol. 12, 2003, pp. 126-134.
Goel et al, "Plasticity within the Antigen-Combining Site May Manifest as Molecular Mimicry in the Humoral Immune Response", J. Immunol. 173: 7358-7367, 2004.
Haussecker, Dirk "Is Dendrimer-siRNA Delivery Reaching Critical Mass?", htt12://rnaithera12eutics.blogs 12ot.com/2009/09/is-dendrimer-sirna-delive!Yreachina. html Sep. 30, 2009, 17 pgs.
Hawtin, et al., "Voreloxin Is an Anticancer Quinolone Derivative that Intercalates DNA and Poisons Topoisomerase II", PLoS One vol. 5 Issue 4 e10186, Apr. 2010, 10 pages.
Hayes et al., "A prolonged and exaggerated wound response with elevated ODC activity mimics early tumor development", Carcinogenesis, vol. 32, 2011, pp. 1340-1348.
Hayes et al., "Elevated levels of ornithine decarboxylase cooperate with Raf/ERK activation to convert normal keratinocytes into invasive malignant cells", Oncogene, vol. 25, 2006, pp. 1543-1553.
Herfs, et al., "A discrete population of squamocolumnar junction cells implicated in the pathogenesis of cervical cancer", PNAS, 2012, vol. 109, No. 26, pp. 10516-10521, and Supporting Information, 10 pgs.
Hsu et al., "Aggressive melanoma cells escape from BMP7-mediated autocrine growth inhibition through coordinated Noggin upregulation", Lab Invest., vol. 88, 2008, pp. 842-855.

Ikeda et al, "The Monoclonal Antibody nBT062 Conjugated to Cytotoxic Maytansinoids Has Selective Cytotoxicity Against CD138-Positive Multiple Myeloma Cells In vitro and In vivo", Clin Cancer Res, 2009, 15(12): 4028-4037.
Jamora et al., "Links between signal transduction, transcription and adhesion in epithelial bud development", Nature, vol. 422, 2003, pp. 317-322.
Jejurikar and Kuzon. Satellite cell depletion in degenerative skeletal muscle. Apoptosis 2003; 8: 573-578.
Juliano, "Peptide-oligonucleotide conjugates for the delivery of antisense and siRNA", Curr Opin Mol. Ther., 2005, vol. 7(2), pp. 132-136.
Ke et al., Two design strategies for enhancement of multilayer-DNA-origami folding: underwinding for specific intercalator rescue and staple-break positioning. Chem. Sci. 3, 2587-2597 (2012).
Keen et al., Publication date:Oct. 1, 2008, "A step towards a new targeted nanotherapy for pancreatic cancer", Source: Cancer biology & therapy, Oct. 1, 2008, Landes Bioscience, US, Interregnum: ISSN 1538-4047, DOI: https://dx.doi.org/10.4161/cbt.7.10.6758, Source details: vol. 7, Nr.:10, XP055483288, pp. 1591-1592.
Kobielak et al., "Loss of a quiescent niche but not follicle stem cells in the absence of bone morphogenetic protein signaling", Proc. Natl. Acad. Sci., vol. 104, 2007, pp. 10063-10068.
Lang et al., "Pax3 functions at a nodal point in melanocyte stem cell differentiation", Nature, vol. 433, 2005, pp. 884-887.
Leask et al. Matrix contraction by dermal fibroblasts requires syndecan 4: Insights into pathological scarring in chronic fibrotic disease. The FAS EB Journal. 2006;20:A 1098). Abstract 688.8.
Li et al, Controlled assembly of dendrimer-like DNA, Nature Materials, 3(1):38-42 (Jan. 2004).
Li et al, Multiplexed detection of pathogen DNA with DNA-based fluorescence nanobarcodes, Nature Biotechnology, 23(7):885-9 (Jul. 2005).
Lisgarten, et al., "The antimalarial and cytotoxic drug cryptolepine intercalates into DNA at cytosine-cytosine sites", Nature Structural Biology vol. 9 No. 1, Jan. 2002, 57-60.
Lloyd et al., "Modelling the human immune response: performance of a 1011 human antibody repertoire against a broad panel of therapeutically relevant antigens", Protein Engineering, Design & Selection 2009, 22: 159-168 (Year: 2009).
Lowe et al, Multiplexed, particle-based detection of DNA using flow cytometry with 3DNA dendrimers for signal amplification, Cytometry A, 60(2):135-44 (Aug. 2004).
Lugini et al., "Cannibalism of Live Lymphocytes by Human Metastatic but Not Primary Melanoma Cells", Cancer Res., vol. 66, 2006, pp. 3629-3638.
Marchan et al., "Diels-Alder cycloadditions in water for the straightforward preparation of peptide-oligonucleotide conjugates", Nucleic Acids Research, 2006, vol. 34(3), pp. 1-9.
Melikov et al, Arginine-dch cell penetrating peptides: from endosornal uptake to nuclear delivery, Cellular and Molelecular Life Sciences, 62(23):2739-49 (Dec. 2005).
Mizuno et al., "Simultaneous Delivery of Doxorubicin and Immunostimulatory CpG Motif to Tumors Using a Plasmid DNA/Doxorubicin Complex in Mice," Journal of Controlled Release (Jan. 25, 2010) vol. 141, No. 2, pp. 252-259.
Montanaro et al., "Skeletal muscle engraftment potential of adult mouseskin side population cells", Proc. Natl. Acad. Sci., vol. 100, 2003, pp. 9336-9341.
Mora et al, Dendrimer FISH detection of single-copy intervals in acute promyelocytic leukemia, Molecular and Cellular Probes, 20(2): 114-20 (Apr. 2006).
Mora et al., "Protein Detection Enhanced by 3DNA Dendrimer Signal Amplification," BioTechniques (2008) vol. 44, No. 6, pp. 815-818.
Murciano et al, ICAM-directed vascular immunotargeting of antithrombotic agents to the endothelial luminal surface, Blood, 101(10):3977-3984 (May 2003).
Muro et al, A novel endocytic pathway induced by clustering endothelial ICAM-1 or PECAM-1, Journal of Cell Science, 116 Pt 8 :1599-609 Apr. 2003).

(56) References Cited

OTHER PUBLICATIONS

Muro et al, Control of intracellular trafficking of ICAM-1-targeted nanocarriers by endothelial Na+/H+ exchanger proteins, American Journal of Physiology. Lung Cellular and Molecular Physiology, 290 (5):L809-I 7 (May 2006).

Muro et al, ICAM-1 recycling in endothelial cells: a novel pathway for sustained intracellular delivery and prolonged effects of drugs, Blood, 105(2):650-8 (Jan. 2005).

Muro et al, Lysosomal enzyme delivery by ICAM-1-targeted nanocarriers bypassing glycosylation- and clathrin-dependent endocytosis, Molecular Therapy, 13(1):135-41 (Jan. 2006).

Muro et al, Slow intracellular trafficking of catalase nanoparticles targeted to ICAM-1 protects endothelial cells from oxidative stress, American Journal of Physiology. Cell Physiology, 285(5):C1339-47 (Nov. 2003).

Muro, (May 2014) "A DNA Device that Mediates Selective Endosomal Escape and Intracellular Delivery of Drugs and Biologicals", Advanced Functional Materials, 2014, 24(19), pp. 2899-2906.

Nagamoto, T., et al. "Alpha-smooth muscle actin expression in cultured lens epithelial cells." Invest Ophthalmol Vis Sci. Apr. 2000;41 (5): 1122-9.

Oehlke et al., "Cellular uptake of antisense oligonucleotides after complexing or conjugation with cell-penetrating model peptides", Eur. J. Biochem., 2002, vol. 269, pp. 4025-4032.

Oh et al, Subtractive proteomic mapping of the endothelial surface in lung and solid tumours for tissue-specific therapy, Nature 429(6992):629-35 (Jun. 2004).

Owens et al., "The Role of Smads in Skin Development", J. Invest. Dermatol., vol. 128, 2008, pp. 783-790.

Papadakis et al., Publication date: Mar. 1, 2004, "Promoters and control elements: designing expression cassettes for gene therapy.", Source: Current Gene Therapy, Mar. 1, 2004, Bentham Science Publishers Ltd., NL, Interregnum: ISSN 1566-5232, DOI: https://dx.doi.org/10.2174/1566523044578077, Source details: vol. 4, Nr.:1, XP009159935, pp. 89-113.

Patil, Mahesh L. "Surface-Modified and Internally Cationic Polyamidoamine Dendrimers for Efficient siRNA Delivery", Bioconjugate Chem. vol. 19 Jun. 25, 2008, 1396-1403 (XP002617104).

Peng et al, "Nanoparticulate Delivery of Suicide DNA to Murine Prostate and Prostate Tumors", The Prostate 67: 855-862, 2007.

Peng et al., Publication date: Oct. 1, 2011, "Epithelial cell-targeted transgene expression enables isolation of cyan fluorescent protein (CFP)-expressing prostate stem/progenitor cells", Source: Transgenic Research, Oct. 1, 2011, Springer Netherlands, NL, Interregnum: ISSN 0962-8819, DOI: https://dx.doi.org/10.1007/s11248-010-9478-2, Source details: vol. 20, Nr.:5, XP055483317, pp. 1073-1086.

Pye et al., "Dermal fibroblasts participate in the formation of new muscle fibres when implanted into regenerating normal mouse muscle", J. Anat., vol. 198, 2001, pp. 163-173.

Rendl et al., "Molecular Dissection of Mesenchymal-Epithelial Interactions in the Hair Follicle", PLOS Biol., vol. 3, 2005, pp. e331.

Rizzo et al, "Prostate epithelial stem cells", Cell Proliferation 38: 363-374, 2005.

Rogers et al., "Peptide conjugates for chromosomal gene targeting by triplex-forming oligonucleotides", Nucleic Acids Research, 2004, vol. 32(22), pp. 6595-6604.

Sampathkumar et al, "Dendrimers in Cancer Treatment and Diagnosis", Nanomaterials for Cancer Diagnosis 7: 43 pages, in Nanotechnologies for the Life Sciences, C. S. Kumar (Ed.), Wiley-VCH Verlag GmbH & Co. KGaA, 2007, DOI:10.1002/9783527610419.ntls0071.

Sharov et al., "Bone Morphogenetic Protein Antagonist Noggin Promotes Skin Tumorigenesis via Stimulation of the Wnt and Shh Signaling Pathways", Am. J. Pathol., vol. 175, 2009, pp. 1303-1314.

Showalter et al, ""Nanoparticulate delivery of diphtheria toxin DNA effectively kills mesothelin expressing pancreatic cancer cells", Source: Cancer Biology & Therapy", Cancer Biol. & Therapy 7 ( 10) 2008: DOI: https://dx.doi.org/10.4161/cbt.7.10.6562; 1584-1590.

Singh et al, On the gene delivery efficacies of pH-sensitive cationic lipids via endosomal protonation: a chemical biology investigation, Chemistry & Biology, 11(5):713-23 (May 2004).

Sneddon et al., "Bone morphogenetic protein antagonist gremlin 1 is widely expressed by cancer-associated stromal cells and can promote tumor cell proliferation", Proc. Natl. Acad. Sci., vol. 103, 2006, pp. 14842-14847.

Stayton et al, 'Smart' delivery systems for biomolecular therapeutics, Orthodontics and Craniofacial Research, 8 (3):219-25 (Aug. 2005).

Stears et al., "A Novel, Sensitive Detection System for High-Density Microarrays Using Dendrimer Technology." Physiol. Genomics (2000) vol. 3, pp. 93-99.

Stetsenko et al., "Efficient Conjugation of Peptides to Oligonucleotides by 'Native Ligation'", J. Org. Chem., 2000, vol. 65(16), pp. 4900-4908.

Suk et al, Gene delivery to differentiated neurotypic cells with RGD and HIV Tat peptide functionalized polymeric nanoparticles, Biomaterials, 27(29):5143-50 (Oct. 2006).

Tamaki et al. Identification of myogenic-endothelial progenitor cells in the interstitial spaces of skeletal muscle. J Cell Biol. May 13, 2002; 157(4):571-7.

Tan et al., "Designer Tridentate Mucin 1 Aptamer for Targeted Drug Delivery," Journal of Pharmaceutical Sciences (May 1, 2012) vol. 101, No. 5, pp. 1672-1677.

Thawani et al., "Bone Morphogenetic Proteins and Cancer Review of the Literature", Neurosurgery, vol. 66, 2010, pp. 233-246.

Tong et al, "Identification of HPV-16 in Borderline Mucinous Cystic Neoplasm of Pancreas", Int. J. Biomed. Sci. 3(1): 72-75, 2007; abstract only.

Tung et al., "Preparation and Application of Peptide-Oligonucleotide Conjugates", Bioconjugate Chem., 2000, vol. 11 (5), pp. 605-618.

Walker, J., et al. "Unique precursors for the mesenchymal cells involved in injury response and fibrosis." Proc Natl Acad Sci US A. Aug. 3, 2010; 107(31):13730-5. Epub Jul. 15, 2010.

Walker, J.L., et al. "Activation of SRC kinases signals induction of posterior capsule opacification." Invest Ophthalmol Vis Sci. May 2007;48(5):2214-23.

Wei et al., "A Bio-Abiotic Interface Constructed by Nanoscale DNA-Dendrimer and Conducting Polymer for Ultra-Sensitive Bio-Molecular Diagnosis," Small (2009) vol. 5, No. 15, pp. 1784-1790.

Wolff, I.M., et al. "Migration of Lens Epithelial Cells on the Posterior Lens Capsule is Blocked by Inhibition of Src Family Kinases." Invest Opthalmol Vis Sci. 2005;46:E-Abstract 2868.

Wormstone et al. Hepatocyte Growth Factor Function and c-Met Expression in Human Lens Epithelial Cells Invest Ophthalmol Vis Sci. 2000;41 :4216-4222.

Wormstone, I.M., et al. "Identification of Signalling Pathways Involved in TGFB2 Induced Matrix Contraction of Human Lens Cells." Investigative Opthalmology & Visual Science.May 1, 2005 ;46(8).

Wu et al., "Dendrimers as Carriers for siRNA Delivery and Gene Silencing: A Review", The Scientific World Journal, 2013, vol. 2013, Article ID 630654, pp. 1-16.

Yang et al., "Targeted Disruption of Smad4 in Mouse Epidermis Results in Failure of Hair Follicle Cycling and Formation of Skin Tumors", Cancer Res., vol. 65, 2005, pp. 8671-8678.

Yuen et al., "The prognostic significance of BMP-6 signaling in prostate cancer", (Modern Pathology, 2008, 21: 1436-1443).

Yuhki et al., "BMPR1A signaling is necessary for hair follicle cycling and hair shaft differentiation in mice", Development, vol. 131, 2004, pp. 1825-1833.

Zammit et al. The Skeletal Muscle Satellite Cell: The Stem Cell That Came in From the Cold. J Histochem Cytochem 2006 54: 1177-1190.

Zatsepin et al., "Conjugates of Oligonucleotides and Analogues with Cell Penetrating Peptides as Gene Silencing Agents", Current Pharmaceutical Design, 2005, vol. 11(28), pp. 3639-3654.

(56) References Cited

OTHER PUBLICATIONS

Zhang et al., "Antibody-Linked Spherical Nucleic Acids for Cellular Targeting", Journal of the American Chemical Society, 2012, 134(40), pp. 16488-16491.
Zhang et al., "Bone Morphogenetic Protein Signaling Inhibits Hair Follicle Anagen Induction by Restricting Epithelial Stem/Progenitor Cell Activation and Expansion", Stem Cells, vol. 24, 2006, pp. 2826-2839.
Zhao et al, "DNA Origami Delivery System forCancer Therapy with TunableRelease Properties", ACS Nano 6(10):8684-8691, Sep. 5, 2012.
Zhou, J., et al. "Inhibition of SRC Family Kinases Blocks Formation of Cortical Cataracts in Cultured Chick Embryo Lenses." Annual Meeting of the Association for Research in Vision and Opthamology. May 10, 2002; 2002.
Zhou, J., et al. "SRC Kinase Activation Induces Formation of Lens Opacities Through a Pathway." Annual Meeting of the Association for Research in Vision and Opthamology. May 8, 2003; 2003.
Zuhorn et al, Nonbilayer phase of lipoplex-membrane mixture determines endosomal escape of genetic cargo and transfection efficiency, Molecular Therapy, 11(5):801-10 (May 2005).
Gerhart, J., et al., "Antibody-Conjugated, DNA-Based Nanocarriers Intercalated with Doxorubicin Eliminate Myofibroblasts in Explants of Human Lens Tissue" J_ Pharmacol. Exp_ Ther. (2017) 361 :60-67.
Abderrezak et al., "Dendrimers Bind Antioxidant Polyphenols and cisPlatin Drug," PLoS One (2012) 7(3): e33102. (Year: 2012).
Adhikary, G., et al., "Identification of a Population of Epidermal Squamous Cell Carcinoma Cells with Enhanced Potential for Tumor Formation" PLoS One (2013) 8(12): e84324.
Agarwal et al., "Dextran Conjugated Dendritic Nanoconstructs as Potential Vectors for Anti-Cancer Agent," Biomaterials (2009) 30, pp. 3588-3596.
Al-Ahmadi et al., "miR-29a inhibition normalizes HuR overexpression and aberrant AU-rich mRNA stability in invasive cancer", Journal of Pathology, May 2013, vol. 230, No. 1, 11 pages.
Almenar-Queralt et al, Apical topography and modulation of ICAM-1 expression on activated endothelium, American Journal of Pathology, 147(5):1278-88 (Nov. 2005).
Anderson et al., "A Polymer Library Approach to Suicide Gene Therapy for Cancer," PNAS (Nov. 9, 2004) vol. 101, No. 45, pp. 16028-16033.
Andl et al., "Epithelial Bmpr1a regulates differentiation and proliferation in postnatal hair follicles and is essential for tooth development", Development, vol. 131, 2004, pp. 2257-2268.
Anwer et al, "Targeted Gene Delivery: A Two-Pronged Approach", Crit. Rev. Ther. Drug Carrier Syst. 17(4): 377-424, 2000; abstract only.
Arya et al, Enhanced anti proliferative activity of Herceptin (H ER2)-conjugated gemcitabine-loaded chitosan nanoparticle in pancreatic cancer therapy, Nanomedicine: Nanotechnology, Biology, and Medicine 7: 859-870, 2011.
Ben-Yair et al., "Lineage analysis of the avian dermomyotome sheet reveals the existence of single cells with both dermal and muscle progenitor fates", Development, vol. 132, 2005, pp. 689-701.
Bonazzi et al, Bacterial entry into cells: a role for the endocytic machinery, FEBS Letters, 580(12):2962-7 (May 2006).
Borucki et al., "Suspension Microarray with Dendrimer Signal Amplification Allows Direct and High-Throughput Subtyping of Listeria Monocytogenes with Genomic DNA," Journal of Clinical Microbiology (2005) vol. 43, No. 7, pp. 3255-3259.
Botchkarev et al., "Noggin is required for induction of the hair follicle growth phase in postnatal skin", FASEB J., vol. 15, 2001, pp. 2205-2214.
Botchkarev, V.A., "Bone Morphogenetic Proteins and Their Antagonists in Skin and Hair Follicle Biology", J. Invest. Dermatol., vol. 120, 2003, pp. 36-47.
Chakravarty et al., "Thermal ablation of tumor cells with antibody-functionalized single-walled carbon nanotubes", PNAS, vol. 105, 2008, pp. 8697-8702.

Chang et al., "Aptamer-Conjugated DNA Icosahedral Nanoparticles as a Carrier of Doxorubicin for Cancer Therapy," ACS NANO (Aug. 23, 2011) vol. 5, No. 8, pp. 6156-6163.
Chavali et al., "Oligonucleotide properties determination and primer designing: a critical examination of predictions", Bioinformatics, 2005, vol. 21(20), pp. 3918-3925.
Chen et al. Matrix contraction by dermal fibroblasts requires TGFbeta/ALK5, heparan sulfate containing proteoglycans and MEK/ERK: Insights into pathological scarring in chronic fibrotic disease . . . Am J Pathol 2005, 167:1699-1711.
Chen et al., "Synthesis of Antisense Oligonucleotide-Peptide Conjugate Targeting to GLUT-1 in HepG-2 and MCF-7 Cells", Bioconjugate Chem., 2002, vol. 13(3), pp. 525-529.
Cho et al., "Therapeutic Nanoparticles for Drug Delivery in Cancer" , CLIN, 2008 Cancer Res., vol. 14, pp. 1310-1316.
Conner et al, Regulated portals of entry into the cell, Nature, 422(6927):37-44 (Mar. 2003).
Cornelison et al . Essential and separable roles for syndecans-3 and syndecan-4 in skeletal muscle development and regeneration. Genes & Development 18:2231-2236, 2004.
Cornelison et al. Syndecan-3 and Syndecan-4 Specifically Mark Skeletal Muscle Satellite Cells and Are Implicated in Satellite Cell Maintenance and Muscle Regeneration. Developmental Biology 239, 79-94 (2001).
Dawson et al., "Synthesis of Native Proteins by Chemical Ligation", Ann. Rev. Biochem., vol. 69, 2000, pp. 923-960.
Derfus et al., Targeted quantum dot conjugates for siRNA delivery, 2007, Bioconjugate Chemistry, vol. 18, pp. 1391-1396.
Dermaut et al., "Aberrant lysosomal carbohydrate storage accompanies edocytic defects and neurodegeneration in *Drosophila* benchwarmer", Jcell Biol., vol. 170, 2005, pp. 127-139.
Dhami et al., "Mannose 6-Phosphate Receptor-mediated Uptake Is Defective in Acid Sphingomyelinase-deficient Macrophages", J Biol Chem., vol. 279, 2004, pp. 1526-1532.
Edwards et al., "The Remarkable Flexibility of the Human Antibody Repertoire; Isolation of Over One Thousand Different Antibodies to a Single Protein, BLyS", J Mol Biol. 334(1 ): 103-118 (Year: 2003).
Feng et al., "Enhanced Immune Response and Protective Effects of Nano-chitosan-based DNA Vaccine Encoding T Cell Epitopes of Esat-6 and FL against *Mycobacterium* Tuberculosis Infection", PLoS One, 2013, vol. 8(4), pp. 1-10.
Friedlander, M. "Fibrosis and diseases of the eye." J Clin Invest. Mar. 2007; 117(3):576-86.
Gabbiani, G., "The myofibroblast in wound healing and fibrocontractivediseases", J. Pathol., vol. 200, 2003, pp. 500-503.
Geiszt, "Chronic granulomatous disease: more than the lack of superoxide?", J Leukoc Biol, vol. 69, No. 2, 2001, pp. 191-196.
GenBank, Database accession No. AK298000.
GenBank, Database accession No. AK304337.
GenBank, Database accession No. NM_003750.2.
GenBank, Database accession No. NM_015904.3.
GenBank, Database accession No. NP 002989.
GenBank, Database accession No. NP 002990.
GenBank, Database accession No. NP 055469.
GenBank, Database accession No. NP_001006947.
GenBank, Database accession No. NP_003741.1.
GenBank, Database accession No. NP_056988.3.
GenBank, Database accession No. P46940.
GenBank, Database accession No. Q05DN7.
GenBank, Database accession No. Q5FWG8.
GenBank, Database accession No. Q6P1N4.
GenBank, Database accession No. Q96PA3.
Gerhart et al. (2000) "DNA dendrimers localize MyoD mRNA in presomitic tissues of the chick embryo", J. Cell Biol., 149:825-834.
Gerhart et al. (2011) "Myo/Nog cell regulation of bone morphogenetic protein signaling in the blastocyst is essential for normal morphogenesis and striated muscle lineage specification", Dev. Biol., 359:12-25.
Gerhart et al. (2012) "Myo/Nog cells in normal, wounded and tumor-bearing skin", Dev. Biol., 21 (6):466-8.

(56) References Cited

OTHER PUBLICATIONS

Gerhart, J., et al. "Cells that express MyoD mRNA in the epiblast are stably committed to the skeletal muscle lineage." J Cell Biol. Aug. 13, 2007;178(4):649-60.

* cited by examiner

CELLULAR DELIVERY OF DNA INTERCALATING AGENTS

CROSS REFERENCE TO RELATED APPLICATIONS

This is a continuation application of co-pending U.S. patent application Ser. No. 15/631,226, filed Jun. 23, 2017, which is a divisional application of U.S. patent application Ser. No. 14/778,716, filed Sep. 21, 2015, now abandoned, which is the National Stage entry of International Application No. PCT/US2014/031192, filed Mar. 19, 2014, which claims the benefit of U.S. Provisional Patent Application No. 61/803,863, filed Mar. 21, 2013, the disclosures of which are incorporated herein by reference in their entireties.

CROSS-REFERENCE TO SEQUENCE LISTING

The Sequence Listing text file created Jun. 18, 2014 (874 B) and identified as "00869100.txt" is hereby incorporated by reference.

TECHNICAL FIELD

The invention relates to delivery of active agents to cells using DNA carriers, wherein the active agent intercalates into the DNA of the carrier. The DNA carrier may further include a targeting agent that binds the DNA carrier to a particular cell type, thus facilitating delivery of the intercalated active agent to the cell.

BACKGROUND

Non-covalent interactions between active agents and DNA generally occur either by groove binding or intercalation. In particular, the field of anti-cancer therapies has produced several chemotherapeutic drugs that interact with DNA by intercalation, a process that involves insertion of a planar drug molecule between DNA base pairs. This results in a decrease in the helical turn and lengthening of the DNA. The association constants of intercalation may be $10^5$ to $10^{-11}$ $M^{-1}$ due to favorable hydrophobic bonding, ionic bonding, hydrogen bonding and van der Waals forces. Intercalation is generally associated with fused ring structures, but non-fused ring systems are also known. Intercalation is recognized as a significant contributor to successful use of these compounds as antitumor, antineoplastic, antimalarial, antibiotic, and antifungal agents, because most are genotoxic, particularly when basic, cationic, or electrophilic functional groups are present.

DNA dendrimers are complex, highly branched molecules built from interconnected natural or synthetic monomeric oligonucleotide subunits. A DNA dendrimer is constructed from DNA monomers, each of which is made from two DNA strands that share a region of sequence complementarity located in the central portion of each strand (aka the "waist"), but have four non-complementary single-stranded "arms" for hybridization to the "arms" of other monomers. Monomers are assembled into dendrimers beginning with a single monomer which is hybridized to additional monomers via the complementary arms. Additional layers are added in a similar manner by hybridization of monomers to the arms of the monomers in the previous layer. By varying the number of layers and which arms are hybridized to additional monomers, DNA dendrimers of different sizes and shapes are produced. In order to prevent DNA dendrimers from falling apart over time, chemical "spot welds" may be added to the growing assembly using UV light via the intercalation and activation of psoralen cross-linkers. Dendrimers are typically purified according to their size and molecular weight on denaturing sucrose gradients after ultracentrifugation.

DNA dendrimers may also be covalently or non-covalently bound to a large variety of different types of molecules and particles, generally via linkage to the un-hybridized arms present on the outer layer. These molecules and particles may be signaling and targeting devices on the DNA dendrimers, allowing targeting of DNA dendrimers to specific molecular targets and detection of the binding of the dendrimers to the targets via detection of the signaling moieties. Signal generating moieties include a large number of fluorescent dyes, haptens, enzymes and other molecular materials, as well as particles such as gold nanoparticles and quantum dots. Targeting devices include DNA, RNA and PNA oligonucleotides, antibodies, antibody fragments, haptens, aptamers, peptides and others. Because the outside layer of monomers contains many un-hybridized arms, DNA dendrimer constructs act as signal amplifiers in a large variety of in-vitro applications, generally for the detection of specific nucleic acids and proteins, but also as detection devices in electronic devices. Applications include signal amplification on DNA and protein microarrays, ELISAs and ELOSAs, Luminex bead assays, in-situ hybridization, and others. The use of labeled and targeted DNA dendrimers has been extensively published in research studies and these materials are available as commercial research products sold or produced by Genisphere LLC (Hatfield, PA).

DNA dendrimers have also been shown to have potential use as delivery and transfection devices in both in-vitro and in-vivo applications. See, e.g., U.S. 2005/0089890, WO 2008/147526 and WO 2010/017544, each of which is incorporated by reference in its entirety. Specifically, DNA dendrimers are bound with targeting devices (e.g. an antibody specific for a cell surface feature capable of eliciting an cellular endocytotic internalization event) which bind to surface features on cells targeted to receive the delivery of a cargo (e.g. a drug). Cargos passively associated with the targeted DNA dendrimer enter the cell simply by spatial association with the dendrimer, but cargos may also be bound to the dendrimer via a number of attachment strategies, including linking to the outer arms.

SUMMARY

The present invention relates to an improved method for delivery of active agents to cells using DNA carriers. The DNA carrier comprises DNA, at least a portion of which is in double-stranded form, and an active agent that intercalates in the double-stranded DNA. In certain embodiments the DNA carrier also comprises a targeting agent that binds to a molecule, cell, or tissue where the active agent is to be delivered. In particular embodiments, the DNA carrier is a DNA dendrimer having the active agent intercalated in the double-stranded portions of the dendrimer. Upon binding of the DNA carrier to the targeted molecule, cell or tissue, the dendrimer is internalized by cells into the endosomes where the acidic pH facilitates release of the active agent from the DNA to produce a cytotoxic or other biological effect.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

In a first aspect, the invention relates to synthetic DNA carriers for delivery of intercalating active agents to cells or tissues, wherein the DNA is wholly or partially double-stranded, and the DNA carrier comprises an active agent intercalated in the double-stranded portions of the DNA. The oligonucleotide component of the synthetic DNA carrier may be a linear or a branched oligonucleotide. Each double-stranded DNA portion of the DNA carrier is 5 bp in length or longer, for example about 20-35 bp, about 35-50 bp, about 50-100 bp, or about 100-200 bp. The synthetic DNA carriers are constructed in vitro and preferably comprise multiple double-stranded portions to increase the load of the active agent. Examples of synthetic DNA carriers comprising multiple double-stranded portions include DNA dendrimers. If the synthetic DNA carrier comprises a linear oligonucleotide, the oligonucleotide may comprise a single double-stranded portion or multiple double-stranded portions. The overall length of such linear oligonucleotides in the DNA carriers is typically at least 10 nt, for example 10-20 nt, 10-50 nt, 10-80 nt, 10-150 nt, or 10-200 nt in length.

In one embodiment, the synthetic DNA carrier may further comprise a targeting agent that binds to a selected cell or tissue type to bind the DNA carrier to the selected cell or tissue type, thus facilitating delivery of the active agent to the selected cell or tissue type. Binding of the targeting agent to the selected cell or tissue type may be via binding of the targeting agent to a cell surface protein or cell surface receptor. Suitable targeting agents include antibodies, ligands or peptides that bind to the cell surface protein or cell surface receptor. The targeting agent is typically linked to the DNA dendrimer arms either covalently or non-covalently (e.g., the targeting agent is linked to an oligonucleotide that is complementary to a dendrimer arm and hybridized to the dendrimer arm).

Examples of cell surface receptors and proteins that may be targeted by the targeting agent include the transferrin receptor (TfR/CD71), the HIV-1 envelope glycoprotein (Env), malarial antigen markers, and the folate receptor. Preferably, the cell surface receptor or protein is specifically expressed on infected, damaged or diseased cells, or is overexpressed on infected, damaged or diseased cells. Specific examples of targeting agents include an anti-transferrin antibody or a TfR-targeting peptide such as THRPPMWSPVWP (SEQ ID NO:1) that binds to the transferrin receptor, which is overexpressed in various cancers. As an example, the targeting agent may also be the G8 monoclonal antibody which binds to a protein of approximately 170 kDa found on the surface of Myo/Nog cells and their derivatives. Myo/Nog cells are identified by expression of mRNA for the skeletal muscle specific transcription factor MyoD, the bone morphogenetic protein (BMP) inhibitor noggin and the cell surface G8 epitope. Other examples of useful targeting moieties include those that bind to PDGF receptor, EGFR family receptors, ICAM, CD receptors, MMP-9, interleukin receptors, folic acid receptor, and others known in the art.

In another embodiment, the active agent intercalated in the double-stranded portions of the DNA carrier is a chemotherapeutic agent, an anti-infective agent, an antimalarial agent, and antiviral agent or an antifungal agent. Specific examples of such agents include berberine (antifungal, antineoplastic), acridines (e.g., proflavine or quinacrine, antiseptic), cancer chemotherapeutics (e.g., daunomycin, doxorubicin, daunorubicin, dactinomycin, cisplatin, carboplatin, voreloxin), cryptolepine (antimalarial cytotoxic) and thalidomide (treatment of multiple myeloma).

In any of the foregoing embodiments, the DNA carrier may comprise a DNA dendrimer, including a 2-layer, 4-layer, 6-layer or 8-layer DNA dendrimer. The size of the DNA dendrimer is selected as needed to facilitate delivery of the active agent to cells and tissues (e.g., via the circulatory system or local injection), and to maximize uptake of the DNA carrier by the cell. In general, the DNA carrier comprises about 3-216 oligonucletoide single strands.

In a second aspect, the invention relates to pharmaceutical compositions comprising the DNA carrier in any of the foregoing embodiments and at least one pharmaceutically acceptable excipient. The pharmaceutically acceptable excipients are any suitable vehicle which can be used to formulate the DNA carriers for administration to a patient, cells or tissues to achieve a therapeutic or other biological result. The excipients are selected from those excipients that are compatible with double-stranded DNA (i.e., they will not denature the DNA carrier prior to delivery to the selected cell or tissue) as well as compatible with the active agent and the targeting agent, if present. Such pharmaceutically excipients include physiological buffers, saccharides and oligosaccharides, stabilizers, thickeners, lubricants, waxes, chelating agents, surfactants, diluents, anti-oxidants, binders, preservatives, coloring agents, emulsifiers, lipid micelles, or other conventional constituents of a pharmaceutical formulation. In certain embodiments the pharmaceutical composition is formulated for parenteral delivery to a patient, for example by injection or infusion. In this case it is preferable that the DNA carrier comprises a targeting agent so that the DNA carrier is directed from the circulation to the desired cell or tissue type. In other embodiments, the pharmaceutical composition may be adapted for oral administration or for local administration to the cell or tissue where delivery of the active agent is desired (e.g., topical formulations).

In a further aspect, the invention relates to methods of making the DNA carriers described in any of the foregoing embodiments. In one embodiment, the DNA carriers are assembled by hybridizing single-stranded DNA to form wholly or partially double-stranded DNA, and combining the wholly or partially double-stranded DNA with the active agent under conditions to allow the active agent to intercalate into the double-stranded portions. Excess active agent is removed, for example by chromatography, to produce the DNA carrier. In a specific embodiment, chromatography to remove excess active agent is performed using a spin column.

In an alternative embodiment, the active agent may be incorporated in the DNA carrier during hybridization of the single-stranded DNA to assemble the wholly or partially double-stranded DNA, followed by removal of excess active agent as described above.

In a further embodiment, the methods of making the DNA carriers comprise assembly of a DNA dendrimer, combining the DNA dendrimer with the active agent under conditions to allow the active agent to intercalate into the double-stranded portions of the DNA dendrimer, and removing excess active agent, for example by chromatography (e.g., a spin column).

In a specific embodiment, in which the DNA carrier is linked to a targeting agent, the DNA carrier is assembled from single-stranded DNA to form wholly or partially double-stranded DNA, and the targeting agent is linked to the assembled DNA. The linkage of the targeting agent to the DNA may be accomplished by covalent attachment as is known in the art, or it may be a non-covalent linkage such as hybridization. Such methods include, for example, linkage via disulfide bonds, N-hydroxysuccinimide (NHS) ester dependent condensation reactions, bifunctional cross-linking, use of polycationic compounds to bridge the targeting agent to the DNA carrier via charge-charge interactions, or direct or indirect hybridization to the DNA carrier as described in WO2010/017544. For example, a single stranded capture oligonucleotide is appended to the arms of a DNA dendrimer, and single-stranded oligonucleotides complementary to the capture sequence are linked to the targeting agent. The complementary sequence on the targeting agent is hybridized to the capture sequence on the DNA dendrimer to link the targeting agent to the DNA dendrimer. The hybridized capture and complementary sequences may optionally be cross-linked. The active agent may be incorporated in the DNA carrier during assembly of the wholly or partially double-stranded DNA or after linkage of the targeting agent to the DNA carrier. If the targeting agent is hybridized to the DNA carrier via a capture sequence, as described above, the double-stranded DNA formed by the linkage can also intercalate the active agent.

In an alternative embodiment of making a DNA carrier linked to a targeting agent, a single-stranded oligonucleotide is attached to the targeting agent in a first step, and then hybridized to a complementary single-stranded oligonucleotide sequence to form the wholly or partially double-stranded DNA of the DNA carrier.

In any of the foregoing methods of making the DNA carriers, the DNA dendrimer may be assembled by any of the methods known in the art, for example as described by T. W. Nilsen, et al. *J. Theor. Biol.* (1997) 187, 273-284.

In yet a further aspect, the invention relates to methods of delivering an active agent to cells or tissues comprising contacting the cells or tissues with a DNA carrier according to any of the foregoing embodiments such that the DNA carrier is taken up by the cell, and the active agent is released inside the cell to produce a cytotoxic or other biological effect on the cell. The cells or tissues may be contacted with the DNA carrier in vivo or in vitro. If cells are contacted with the DNA carrier in vitro, the cells will typically be in cell culture and the DNA carrier is added to the culture medium, incubated with the cells for a period of time to allow binding to the cell surface, and the excess DNA carrier is removed. After sufficient time for endocytosis and release of the active agent, the cytotoxic or biological activity of the active agent on the cells can be visualized microscopically. If the cells are contacted with the DNA carrier in vivo, the DNA carrier is administered to the patient or animal via injection, infusion, local administration to the site of desired action, or by other appropriate methods, for a period of time to allow binding to the cell surface and endocytosis. The cytotoxic or biological activity of the active agent released in the cells can be determined by monitoring a physiological response or by microscopic examination of samples of the affected tissues.

In a further aspect, the invention relates to methods of treating a disease or condition by delivering the DNA carriers to a patient in need thereof, using the foregoing in vivo methods of delivery active agents to cells or tissues. For treatment specificity, the targeting agent is generally selected to be specific for the cell type in which the cytotoxic or other biological activity is desired. The active agent is selected to be therapeutically active against the disease or condition being treated, and the DNA carrier is administered to the patient in amount and for a period of time sufficient to treat, cure or improve the symptoms of the disease or condition. Diseases and conditions treatable by administration of the DNA carriers include any disease or condition for which an active agent is available that intercalates into double-stranded DNA. Non-limiting examples include cancer, malaria, fungal diseases, viral diseases, fibrotic diseases, and the like.

To effect treatment, the synthetic DNA carrier may be administered locally to the tissue or cells to be treated, for example by topical application or injection into the tissue or cells. Alternatively, the synthetic DNA carrier may be administered systemically, for example by intravenous injection or infusion, or by oral administration. In either embodiment, a targeting agent linked to the DNA carrier, if present, facilitates binding of the DNA carrier to the cell type to be treated and delivery of the active agent to that cell type.

In a specific embodiment, posterior capsular opacification (PCO) is prevented, or the incidence thereof is reduced, by administration of a DNA carrier comprising DNA dendrimers linked to a monoclonal antibody targeting the G8 epitope, and a DNA-intercalating cytotoxin. PCO occurs in certain adults and children after cataract surgery, and arises from differentiating lens epithelial cells and myofibroblasts that affect the transparency of the capsule surrounding the lens. There is currently no effective treatment for preventing PCO. It has been discovered that myofibroblasts in human lens tissue originate from Myo/Nog cells that express the skeletal muscle specific transcription factor MyoD, the bone morphogenetic protein inhibitor noggin, and a cell surface molecule recognized by the G8 monoclonal antibody (mAb). Depletion of Myo/Nog cells in explant cultures of human lens tissue procured from patients undergoing cataract surgery was accomplished by lysing them with DNA carriers (DNA dendrimers) according to the invention, using the G8 mAb as the targeting agent and intercalated doxorubicin. Myo/Nog cells were specifically eliminated, as shown in the following examples. From this data, it can be extrapolated that the accumulation of myofibroblasts over time would also be prevented.

EXAMPLES

Example 1: Internalization of G8 mAb Conjugated Dendrimers in Rhabdomyosarcoma Cells 2-Layer DNA Dendrimer Preparation:

DNA dendrimers were manufactured as previously disclosed (see, e.g., U.S. Pat. Nos. 5,175,270, 5,484,904, 5,487,973, 6,110,687 and 6,274,723, each of which is incorporated by reference in its entirety). Briefly, a DNA dendrimer was constructed from DNA monomers, each of which is made from two DNA strands that share a region of sequence complementarily located in the central portion of each strand. The two strands anneal to form the monomer the resulting structure can be described as having a central double-stranded "waist" bordered by four single-stranded "arms". This waist-plus-arms structure comprises the basic 3DNA® monomer. The single-stranded arms at the ends of each of the five monomer types are designed to interact with one another in precise and specific ways. Base-pairing between the arms of complementary monomers allows directed assembly of the dendrimer through sequential addition of monomer layers. Assembly of each layer of the dendrimer includes a cross-linking process where the strands of DNA are covalently bonded to each other, thereby forming a completely covalent molecule impervious to denaturing conditions that otherwise would cause deformation of the dendrimer structure. In addition, 38 base oligonucleotides that serve as complementary capture oligos are ligated to the 5' ends of available dendrimer arms via a simple T4 DNA ligase dependent ligation reaction, as follows:

Attaching a Capture Sequence to a DNA Dendrimer:

To attach the G8 momoclonal Antibody (G8mAb) to the DNA Dendrimer, a capture sequence was first ligated to 10-15% of the dendrimer arms. The complementary oligonucleotide to this capture sequence was conjugated to the G8 monoclonal antibody using commercially available chemistry (Solulink, www.solulink.com) and hybridized in a molar ratio to occupy all of the available capture sequences. Approximately 2-5 G8mAbs were attached per dendrimer molecule as summarized below.

Small (15-100 nucleotides) DNA or RNA capture oligonucleotides (or other biochemical analogs) were covalently attached to the ends of the dendrimer arms via a simple nucleic acid ligation reaction utilizing a bridging oligonucleotide that overlaps adjacent portions of the dendrimer arm and the capture oligonucleotide, thereby bridging the capture oligonucleotide to the end of the dendrimer arm. The bridging oligonucleotide overlapped as least 5 bases of each of the adjacent dendrimer arm and capture oligonucleotide sequences to facilitate the ligation activity of a nucleic acid ligase enzyme (preferably T4 DNA ligase enzyme), with at least 7 bases of overlap of each sequence preferred. The bridging oligonucleotide may also serve as a nucleic acid blocker for its complementary sequences when the dendrimer is used for specific targeting of non-dendrimer nucleic acids or other molecules.

The following components were added to a microfuge tube:
1. 2 layer DNA dendrimer (500 ng/µL) in 1×TE buffer 5.4 µL (2680 ng)
2. a(-)LIG-BR7 Bridging oligo (14mer) (50 ng/µL) 2.7 µL (134 ng)
3. 10× Ligase buffer 10.2 µL
4. Nuclease free water 81.7 µL
5. Cap03 capture oligo (38mer) (50 ng/µL) 4.0 µL (200 ng)
6. T4 DNA Ligase (1 U/µL) 10.0 µL (10 units)

The first four reactants were added together, heated to 65° C. and cooled to room temperature. The 5th and 6th reactants were then added and incubated for 45 minutes. The ligation reaction was stopped by adding 2.8 µL of 0.5M EDTA solution. Non-ligated oligonucleotide was removed via the use of 100 k cutoff centrifugal filters (Millipore Corp.), and during the purification washes, the buffer was changed into 1× sterile PBS, pH7.4. The capture oligonucleotide is linked to a first single-stranded surface arm of the dendrimer.

Antibody Attachment and Fluorescent Labeling of the DNA Dendrimer:

In order to target the cell surface and initiate internalization, a G8 monoclonal antibody was coupled to a DNA dendrimer. The G8 monoclonal antibody was covalently attached to an oligonucleotide that is complementary to the capture sequence which was previously ligated to the dendrimer. Briefly, the capture sequence complement (cpl-Cap03), 5'-TTCTCGTGTTCCGTTTGT ACTCTAAGGTG-GATTTTT-3' (SEQ ID NO:2), was covalently coupled using commercial chemistry to G8 monoclonal antibody (Solulink) by the 3' end and purified by HPLC to remove excess reagents. These conjugates were then hybridized to dendrimer capture sequences during the final assembly of the reagents (refer to 3DNA preparation section below). Additionally, a synthetic oligonuclotide (IDT Technologies) complementary to the outer surface arms of the DNA dendrimer was prepared having two fluorescent labels (Cy3), one each on the 3' and 5' prime ends. This oligonucleotide was then hybridized to the outer arms of the above-prepared G8 mAb target dendrimer in an amount equal to 18 moles oligonucleotide to 1 mole DNA dendrimer. The G8 mAb targeted Cy3 labeled DNA dendrimer was used for targeting and internalization studies on Rhabdomyosarcoma cells.

Internalization of the G8 Monoclonal Antibody Conjugated with Cy3 Labeled Dendrimers in Rhabdomyosarcoma Cells:

Human embryonal and alveolar rhabdomyosarcoma cells (cell lines 136 and 2061 from ATCC) were cultured on glass coverslips in 100 mm tissue culture dishes (12 coverslips/plate) in 8 ml medium for 24 hours. The 136 cell line was cultured in DMEM containing 10% fetal bovine serum. The 2061 cell line was cultured in RPMI containing 10% FBS. Coverslips were transferred to 35 mm tissue culture dishes (2 per coverslips/dish) containing 1 ml of the following media:
1. Culture media containing LysoSensor Green DND 189 stock solution (1 mM) (Molecular Probes/Invitrogen) diluted 1:500 in (2 uM working solution).
2. Culture media containing 2 uM LysoSensor plus G8:4n Dendrimer-Cy3 diluted 1:75.

Figure 1A:
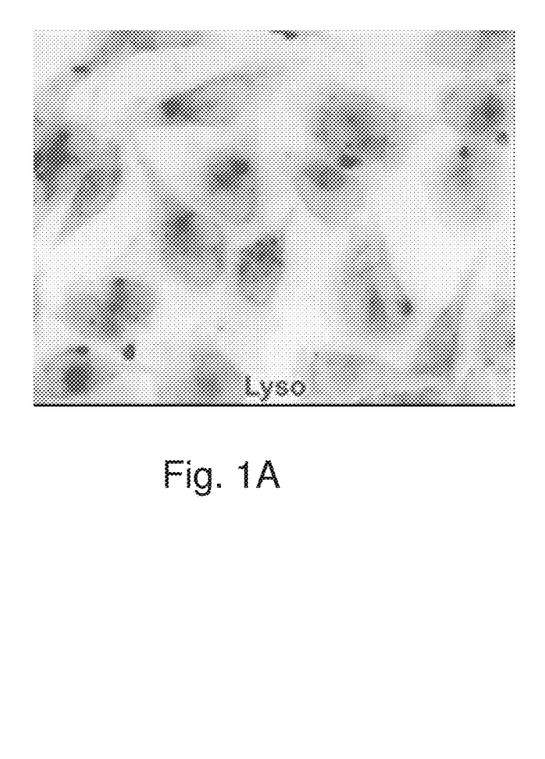
FIG. 1A shows labeling of living cells with LYSOSENSOR dye.
Figure 1B:
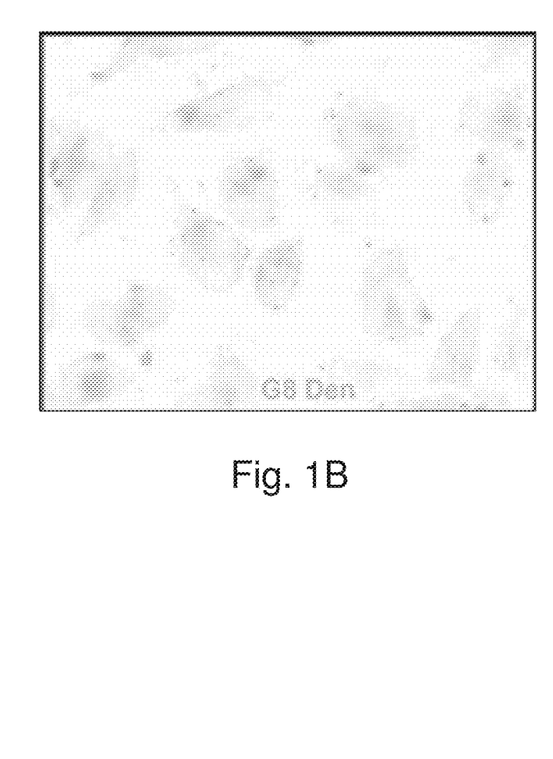
FIG. 1B shows the cells containing internalized dendrimers.
Figure 1C:
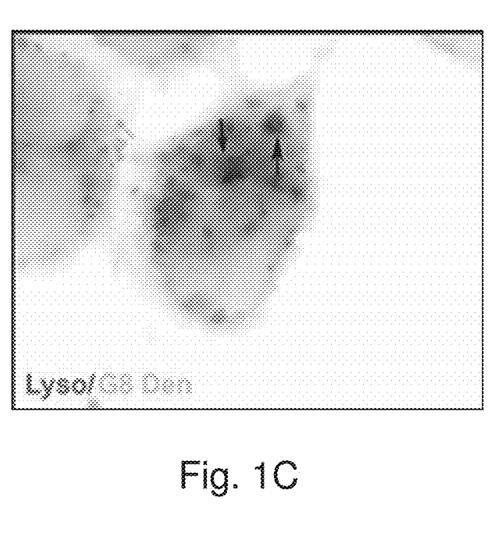
FIG. 1C is a merged image of FIG. 1A and FIG. 1B showing that the dendrimers are internalized into acidic compartments of the cells.

Cells were incubated at 37° C. in 5% $CO_2$ in air for 1 hour. Cells were rinsed in 37° C. PBS and fixed in 2% paraformaldeyde for 10 minutes. Cells were visualized by epifluorescence microscopy. Various dilutions and incubation times were tested. The 1:500 Lysosensor plus 1:75 G8:dendrimer incubated for 1 hour yielded the best results. The results are displayed in FIG. 1A, FIG. 1B and FIG. 1C, which show successful internalization of the labeled dendrimers in Rhabdomyosarcoma cells. FIG. 1A shows cells labeled with LYSOSENSOR dye that fluoresces green at acid pH (concentrated in the dark spots within the cells in FIG. 1A). FIG. 1B shows red fluorescence from Cy3 labeled dendrimers within the cells (concentrated in the dark spots within the cells in FIG. 1B). FIG. 1C is a merged image of FIG. 1A and FIG. 1B, showing co-localization of the green and the red signals, which is visualized as yellow, and shown as the dark spots indicated by the arrows within the cell in FIG. 1C). These results confirm that the G8 mAb coupled to the DNA dendrimer is internalized into acidic compartments of the cell (i.e., the lysosomes).

Example 2: Targeted Depletion of Myo/Nog Cells

2-Layer DNA Dendrimer Preparation:

2-Layer DNA dendrimers were prepared with attached capture sequences as described in Example 1. The capture sequence was ligated to 10-15% of the dendrimer arms.

Attaching G8 mAb to the DNA Dendrimer:

The G8 monoclonal antibody (G8 mAb) was also attached to the DNA Dendrimer as described in Example 1. First, the 3' end of the oligonucleotide complementary to the capture sequence (cplCap03) was conjugated to the G8 monoclonal antibody using commercially available chemistry (Solulink, www.solulink.com). The conjugate was purified by HPLC to remove excess reagents. The capture sequence and the complement of the capture sequence were then hybridized in a molar ratio to occupy all of the available capture sequences. Approximately 2-5 G8 mAbs were attached per dendrimer molecule as summarized below.

Preparation of Doxorubicin Double Stranded Oligonucleotide G8 Antibodies:

1.282 μg of G8 mAb oligonucleotide conjugate (as prepared above) was combined with 1.282 μg of the complementary oligonucleotide sequence (SEQ ID NO:2) and 1500 μl of 200 μM Dox solution, and the final volume was adjusted to 3000 μl using sterile 1×PBS according to the table below. The mixture was incubated at 37° C. for 30 minutes. The final concentration of Dox in 3 mL solution was 100 μM. The reagent was purified using Quickspin High Capacity Sephadex G50 Columns (Roche) according to the manufacture's protocol. Sixteen microliters of 5M NaCl (Life Technologies) was added to achieve an 86 mM NaCl concentration. The final Doxorubicin was determined using fluorometry.

| | Component | Conc | Mass req | Volume (μl) |
|---|---|---|---|---|
| 2 | G8 Ab oligo conjugate (mouse IgM MGW) | 27 ng/μl | 1282.1 | 47.5 |
| 3 | 1X PBS-sterile + Dox | 200 μM | | 1500.0 |
| 4 | 1X PBS-sterile | | | 1452.5 |

Preparation of Doxorubicin 2-Layer Dendrimers (No Targeting):

2 Layer Cap 03 dendrimer (3 μg) was mixed with 1500 ul of 200 μM Dox solution and the final volume was adjusted to 3000 μl using sterile 1×PBS according to the table below and incubated at 37° C. for 30 minutes. The final concentration of Dox in 3 mL solution was 100 μM and final dendrimer concentration was 10 ng/μl). The reagent was purified using Quickspin High Capacity Sephadex G50 Columns (Roche) according to the manufacture's protocol. Sixteen microliters of 5 M NaCl (Life Technologies) was added to achieve an 86 mM NaCl concentration. The final Doxorubicin and Dendrimer concentrations were determined using fluorometry and UV/Vis spectroscopy.

| | Component | Conc | Mass req | Volume (ul) |
|---|---|---|---|---|
| 1 | 2-Layer Cap03 | 359.2 ng/μl | 30000.0 | 83.5 |
| 2 | 1X PBS-sterile + Dox | 200 μM | | 1500.0 |
| 3 | 1X PBS-sterile | | | 1416.5 |
| | | | 3000.000 | μl total vol |

Preparation of Doxorubicin 2-Layer G8 Targeted Dendrimers:

2 Layer Cap 03 dendrimer (3 μg) was mixed with 1.282 μg of G8 mAb oligonucleotide conjugate (as prepared above) and 1500 μl of 200 μM Dox solution, and the final volume was adjusted to 3000 μl using sterile 1×PBS according to the table below. The mixture was incubated at 37° C. for 30 minutes. The final concentration of Dox in 3 mL solution was 100 μM and final dendrimer concentration was 10 ng/μl). The reagent was purified using Quickspin High Capacity Sephadex G50 Columns (Roche) according to the manufacture's protocol. Sixteen microliters of 5 M NaCl (Life Technologies) was added to achieve an 86 mM NaCl concentration. The final Doxorubicin and Dendrimer concentrations were determined using fluorometry and UV/Vis spectroscopy.

| | Component | Conc | Mass req | Volume (ul) |
|---|---|---|---|---|
| 1 | 2-Layer Cap03 | 359.2 ng/μl | 30000.0 | 83.5 |
| 2 | G8 Ab oligo conjugate (mouse IgM MGW) | 27 ng/μl | 1282.1 | 47.5 |
| 3 | 1X PBS-sterile +Dox | 200 μM | | 1500.0 |
| 4 | 1X PBS-sterile | | | 1369.0 |

Targeting Myo/Nog Cells in Human Lens Tissue with the G8 Monoclonal Antibody Conjugated with DNA Dendrimers Intercalated with Doxorubicin:

Human anterior lens tissue removed by capsulorhexis during cataract surgery was collected in DMEM/F12 medium containing 1% Penicillin/Streptomycin (DF). Lens tissue was transferred to an 8-well chamber tissue culture slide containing 240 μl of DF containing the following:

1. No additions
2. G8Ab/Cap03 oligo/CPL—Dox diluted 1:8 in DF
3. 2-layer G8 Ab/Cap03 oligo/Cpl Oligo—diluted 1:8 in DF
4. 2-layer Cap03—high diluted 1:8 in DF Lenses floated in the chamber until they sank to the bottom of the slide. They were cultured for 24 hours in 5% $CO_2$ in air at 37° C. Tissues were rinsed in PBS and fixed in 2% paraformaldehyde for 10 minutes then double labeled with the G8 antibody and an anti-mouse IgM conjugated with Alexa 488 and reagents from the ROCHE TUNEL kit which fluoresce under the rhodamine channel.

The percentages of G8+ and TUNEL+ cells, the percentage of the G8+ cells with TUNEL, and the percentage of TUNEL+ cells with G8 were determined by epifluorescence microscopy. The results are shown in the following table:

| | % G8+ | % TUNEL+ | % G8 with TUNEL | % TUNEL with G8 |
|---|---|---|---|---|
| Untx | 2 | 0.8 | 4 | 13 |
| 2-layer:high dox | 4 | 2 | 0 | 0 |

-continued

|  | % G8+ | % TUNEL+ | % G8 with TUNEL | % TUNEL with G8 |
|---|---|---|---|---|
| G8:2-layer:high dox | 3 | 7 | 100 | 47 |
| G8:ds DNA:high dox | 17 | 19 | 97 | 90 |

Note:
this culture had a lot of cell loss. Only 214 cells left on the lens

Figure 2A:
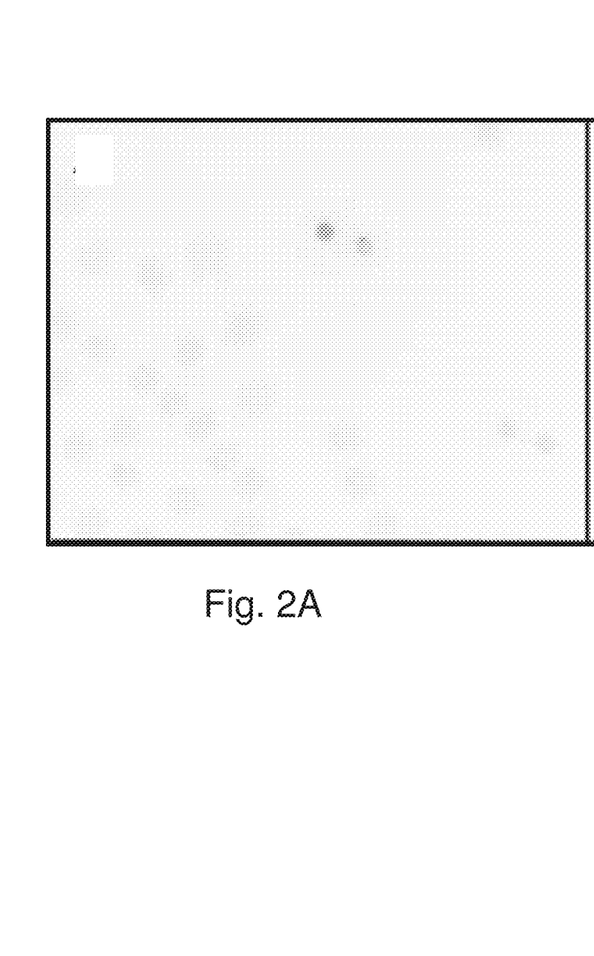
FIGS. 2A-2D show the results of Example 2: untreated cells (FIG. 2A), untargeted Dox dendrimers (FIG. 2B), G8 mAb conjugated Dox dendrimers (FIG. 2C and FIG. 2D).
Figure 2B:
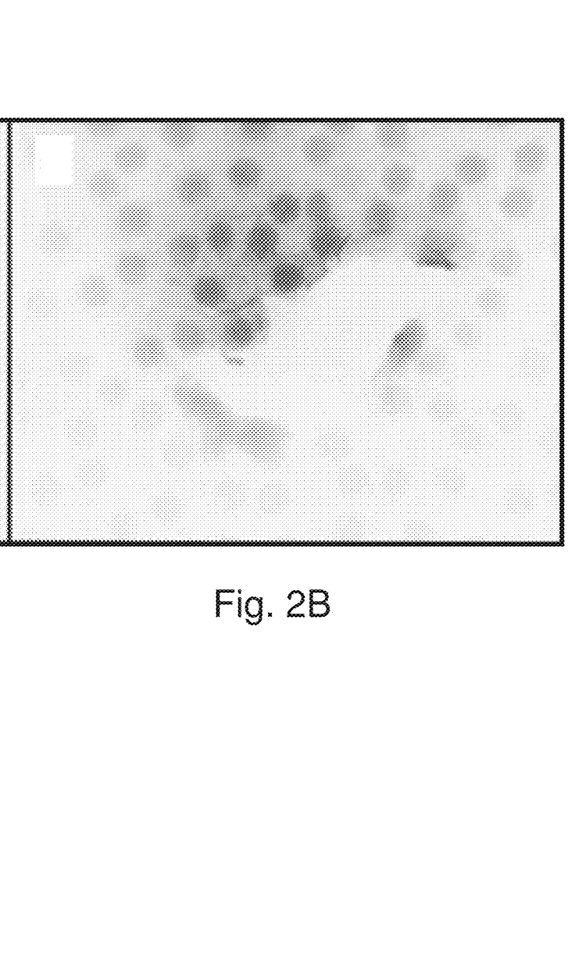
Figure 2C:
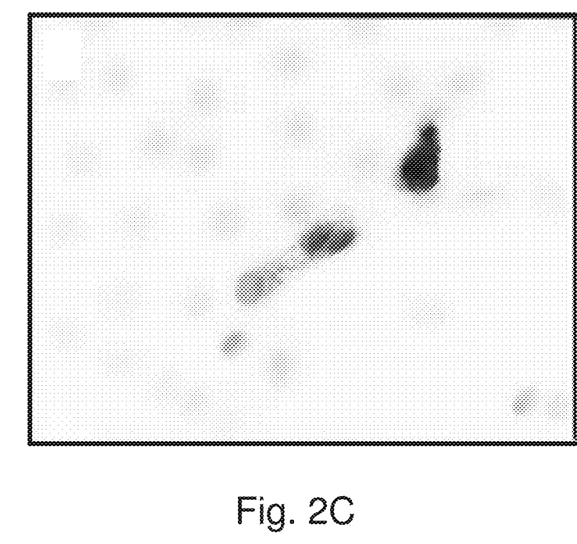
Figure 2D:
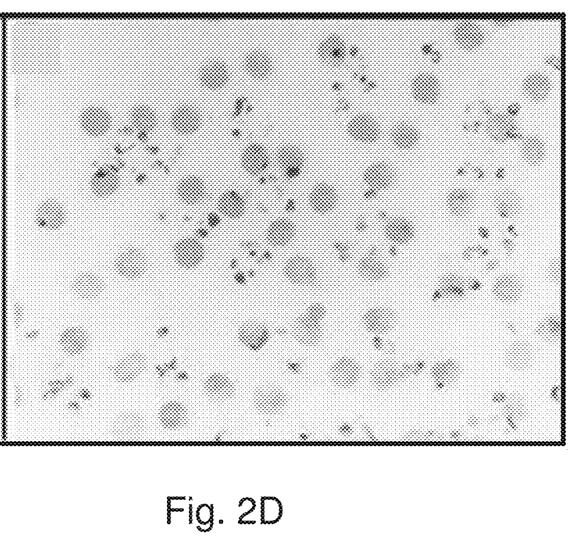

Less than 1% of cells were TUNEL+ in untreated cultures (FIG. 2A). In addition, dendrimers with Dox alone (DNA: DOX) did not induce apoptosis in Myo/Nog cells or G8-negative lens cells (FIG. 2B) as evidenced by a lack of red staining. However, dendrimers conjugated to G8 mAb with Dox (G8:DNA:DOX) specifically induced apoptosis in Myo/Nog cells (FIG. 2C and FIG. 2D, showing two different sections of the culture with different numbers of positive cells). G8-containing cells are stained green, and cells undergoing apoptosis (TUNEL+) are stained red. The TUNEL+ cells in FIG. 2C (red) are indicated by the black spots and the TUNEL+ cells in FIG. 2D (red) are indicated by the dark gray spots. The small black flecks are the green stained G8-containing cells.

The G8 mAb conjugated to the double-stranded oligo with intercalated Dox also specifically induced apoptosis in Myo/Nog cells (data not shown).

Example 3: Targeted Depletion of Pancreatic Tumor Cells

2-Layer DNA Dendrimer Preparation:

2-layer DNA dendrimers are prepared as described in Example 1, including attachment of the capture sequence to 10-15% of the dendrimer arms.

In place of the G8 mAb, a transferrin receptor (TfR/CD71) targeting peptide THRPPMWSPVWP (TfR peptide, SEQ ID NO:1) is linked to the dendrimer. The cplCap03 oligonucleotide, which is complementary to the capture sequence, is covalently coupled by the 3' end to the TfR peptide using commercially available chemistry (Bio-Synthesis, www.biosyn.com), purified by HPLC to remove excess reagents, and hybridized in a molar ratio to occupy all of the available capture sequences. Approximately 2-5 peptides are attached per dendrimer molecule as summarized below.

Preparation of Doxorubicin Double Stranded Oligonucleotide TfR Peptide:

The TfR peptide oligonucleotide conjugate (as prepared above) is hybridized to capture oligonucleotides and combined with Dox as described in Example 1 for preparation of the G8 mAb double-stranded oligonucleotide conjugate with Dox.

Preparation of Doxorubicin 2-Layer Dendrimers (No Targeting):

Doxorubicin 2-layer dendrimers without TfR peptide targeting are also prepared as previously described.

Preparation of Doxorubicin 2-Layer TfR Peptide Targeted Dendrimers:

The 2-layer TfR peptide-targeted dendrimers prepared above were combined with Dox as described in Example 1 for preparation of the G8 mAb dendrimer conjugate with Dox.

In Vivo Mouse Study:

To induce tumor formation in mice $2 \times 10^5$ PAN02-Luc cells (murine pancreatic cancer cells that stably express firefly luciferase) in 20 ml Matrigel are injected directly into the pancreas of B6 mice. Four weeks later, the mice are retro-orbitally injected with 100 μl of 1×PBS (negative control), TfR peptide double-stranded DNA oligonucleotide with doxorubicin, untargeted DNA dendrimer with doxorubicin or TfR peptide targeted DNA dendrimer with doxorubicin. Injections are made two times per week for 2 weeks for a total of 4 doses. The mice are sacrificed 3 days after the last dose, and the tumor, liver, spleen are fixed in 10% formalin for 2 hours, and paraffin-embedded sections are prepared and mounted on slides for further studies. To determine the level of cell death as a result of the treatment, a TUNEL assay is performed using In situ Cell Death Detection Kit (Roche).

Tumors in mice treated with the TfR-targeted DNA dendrimer with intercalated doxorubicin and with the TfR-targeted double-stranded oligonucleotide display significantly more cell death than either the PBS buffer control or the untargeted DNA dendrimer with Dox.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of delivering an active agent to a cell comprising contacting the cell with a pharmaceutical composition, the pharmaceutical composition comprising:
   i) a DNA dendrimer comprising an active agent,
      wherein the DNA dendrimer comprises a plurality of DNA monomers comprising a double-stranded region and four single-stranded arms,
      wherein each DNA monomer comprises a first oligonucleotide molecule and a second oligonucleotide molecule,
      wherein the first oligonucleotide molecule comprises a central portion and two terminal portions,
      wherein the second oligonucleotide molecule comprises a central portion and two terminal portions,
      wherein the central portion of the first oligonucleotide molecule and the central portion of the second oligonucleotide molecule are complementary to form the double-stranded region and the four single-stranded arms; and
   ii) a targeting agent linked to a capture sequence complement, wherein the targeting agent is selected from the group consisting of:
      a) an antibody or peptide that binds to the transferrin receptor, and
      b) an antibody or peptide that binds to G8 antigen; and
      wherein the capture sequence complement is complementary to one or more capture sequences ligated to one or more of the DNA dendrimer single stranded arms.

2. The method of claim 1, wherein the targeting agent is an antibody or peptide that binds to G8 antigen, and the pharmaceutical composition is administered for prevention of posterior capsular opacification or for reducing the incidence of posterior capsular opacification.

3. The method of claim 2, wherein the targeting agent is a monoclonal antibody that binds to G8 antigen and the active agent is doxorubicin.

4. The method of claim 1, wherein the targeting agent is an antibody or peptide that binds to the transferrin receptor, and the pharmaceutical composition is administered for depletion of pancreatic tumor cells.

5. The method of claim 4, wherein the targeting agent is a peptide that binds to the transferrin receptor and the active agent is doxorubicin.

6. The method of claim 1, wherein the composition comprising the DNA dendrimer, comprising an active agent and the targeting agent linked to the DNA dendrimer through a capture sequence complement is internalized by the cells in a subject and the active agent is released into the cell, thereby delivering the active agent to the cell.

7. The method of claim 6, wherein the active agent is intercalated in the double-stranded region of the DNA monomer.

8. The method of claim 1, wherein the contacting the cell comprises administering the composition to a patient.

9. The method of claim 1, wherein the active agent is intercalated in the double-stranded region of the DNA monomers.

10. The method of claim 9, wherein the active agent is intercalated in the double-stranded region of the DNA monomers through hydrogen bonding.

11. The method of claim 1, wherein the active agent is selected from the group consisting of chemotherapeutics, anti-infective agents, antimalarial agents, antiviral agents, and antifungal agents.

12. The method of claim 1, wherein the active agent is berberine, an acridine, daunomycin, doxorubicin, daunorubicin, dactinomycin, cisplatin, carboplatin, or thalidomide.

13. The method of claim 1, wherein 10-15% of the DNA dendrimer single-stranded arms are ligated to a capture sequence of the one or more capture sequences.

14. The method of claim 1, wherein 2-5 targeting agents are attached per DNA dendrimer.

15. A method of delivering an active agent to a cell comprising contacting the cell with a pharmaceutical composition, the pharmaceutical composition consisting essentially of:
   i) a DNA dendrimer comprising an active agent,
      wherein the DNA dendrimer comprises a plurality of DNA monomers comprising a double-stranded region and four single-stranded arms,
      wherein each DNA monomer comprises a first oligonucleotide molecule and a second oligonucleotide molecule,
      wherein the first oligonucleotide molecule comprises a central portion and two terminal portions,
      wherein the second oligonucleotide molecule comprises a central portion and two terminal portions,
      wherein the central portion of the first oligonucleotide molecule and the central portion of the second oligonucleotide molecule are complementary to form the double-stranded region and the four single-stranded arms; and
   ii) a targeting agent linked to a capture sequence complement, wherein the targeting agent is selected from the group consisting of:
      a) an antibody or peptide that binds to the transferrin receptor, and
      b) an antibody or peptide that binds to G8 antigen; and
      wherein the capture sequence complement is complementary to one or more capture sequences ligated to one or more of the DNA dendrimer single stranded arms.

16. The method of claim 15, wherein 10-15% of the DNA dendrimer single-stranded arms are ligated to a capture sequence of the one or more capture sequences.

17. The method of claim 15, wherein 2-5 targeting agents are attached per DNA dendrimer.

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: TfR/CD71 targeting peptide

<400> SEQUENCE: 1

Thr His Arg Pro Pro Met Trp Ser Pro Val Trp Pro
1               5                   10

<210> SEQ ID NO 2
<211> LENGTH: 36
<212> TYPE: DNA
```

```
<213> ORGANISM: Artificial Sequence
<220> FEATURE:
<223> OTHER INFORMATION: Capture Oligonucleotide Complement

<400> SEQUENCE: 2
ttctcgtgtt ccgtttgtac tctaaggtgg attttt                                   36
```